POA PRATENSIS

Filed Aug. 2, 1968 5 Sheets-Sheet 1

INVENTORS

EUGENE W. MAYER

TARAO T. FUCHIGAMI

Strauch Nolan Neale Nies & Kurz
ATTORNEYS

INVENTORS
Eugene W. Mayer
Torao T. Fuchigami

Strauch Nolan Neale Nies + Kurz
ATTORNEYS

INVENTORS
Eugene W. Mayer
Torao T. Fuchigami

Strauch Nolan Neale Nies + Kurz
ATTORNEYS

POA PRATENSIS
Filed Aug. 2, 1968 5 Sheets-Sheet 4
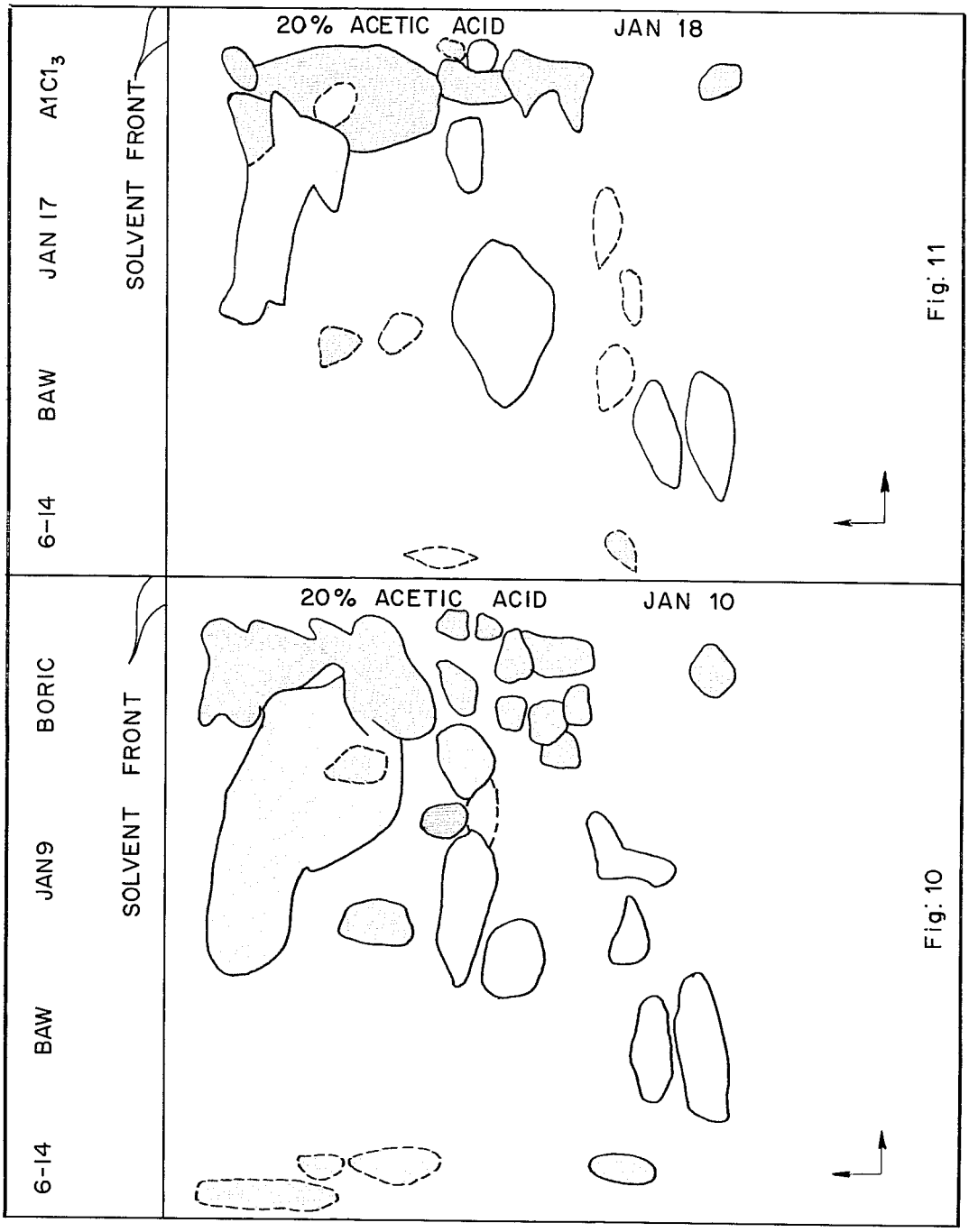
INVENTOR
Eugene W. Mayer
Torao T. Fuchigami
BY Strauch, Nolan, Neale, Nies & Kurz
ATTORNEY INVENTORS
Eugene W. Mayer
Torao T. Fuchigami BY Strauch, Nolan, Neale, Nies & Kurz

ATTORNEY

United States Patent Office

Plant Pat. 3,032

Patented Mar. 2, 1971

3,032

*POA PRATENSIS*

Eugene W. Mayer, Marysville, Ohio, and Torao T. Fuchigami, Long Beach, Calif., assignors to The O. M. Scott and Sons Company, Marysville, Ohio

Filed Aug. 2, 1968, Ser. No. 749,888

Int. Cl. A01h *5/00*

U.S. Cl. Plt.—88 1 Claim

ABSTRACT OF THE DISCLOSURE

A variety of *Poa pratensis* which is capable of producing turfs of superior quality. The variety exhibits good color, high density, and superior vigor and rhizome formation and is unusually resistant to the debilitating effects of high temperature and to turf diseases such as *Fusarium roseum,* Helminthosporium spp, and *Ustilago striiformis.*

The present invention relates to a new and distinct variety of *Poa pratensis* which has been given the designation "Ba 61–24 Kentucky bluegrass." The foundation plant of the variety was selected from cultivated plots by the applicant and propagated first in California and then in other locations.

Ba 61–24 Kentucky bluegrass reproduces asexually both by agamospermy and vegetatively. All asexually reproduced Ba 61–24 Kentucky bluegrass offspring show complete conformity with the mother plant.

The novel Kentucky bluegrass described herein has a number of highly desirable characteristics including good color, a robust nature, rapid propagation, good resistance to turf diseases and to high temperatures and other environmental stress, and the capability of producing a dense turf. Because of this unusual combination of desirable characteristics Ba 61–24 Kentucky bluegrass is capable of producing turfs of significantly higher quality than can be established from other, commercially available varieties of *Poa pratensis.*

Another unique characteristic of Ba 61–24 Kentucky bluegrass is that it gives excellent performance in the so-called "transition zone" for grasses. This is extremely important since, in the areas in this zone, it is very difficult to establish and maintain other species of either northern or southern grasses.

In conjunction with the foregoing, the casual pathogen *Fusarium roseum* is responsible for a turf disease which is very serious in the transition zone. Ba 61–24 has proved to have a high degree of resistance to this organism which is entirely unexpected. Similarly, Ba 61–24 has been found to have a high degree of resistance to the casual organisms Helminthosporium spp and *Ustilago striiformis,* both of which cause widespread damage to bluegrass turfs.

It is our primary object to provide a new and novel variety of *Poa pratensis* having the desirable characteristics described above. Other objects together with further novel features and other desirable attributes of Ba 61–24 Kentucky bluegrass will become apparent from the ensuing detailed description of this variety in conjunction with the accompanying drawing, in which:

FIGS. 10–13 are diagrammatic sketches of thin layer chromatograms of the phenolic constituents of Ba 61–24 bluegrass.

Figure 1:
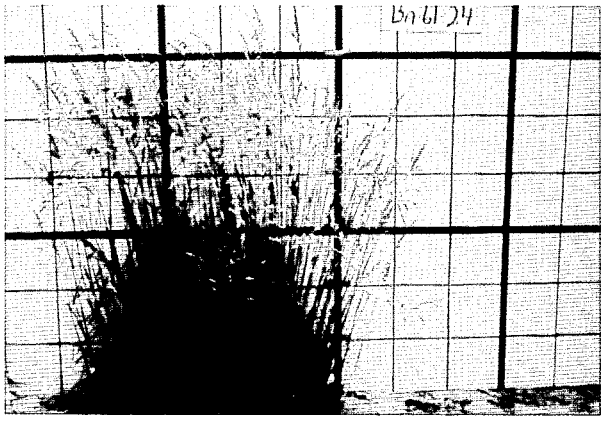
FIG. 1 illustrates a mature Ba 61–24 Kentucky bluegrass clone.
Figure 2:
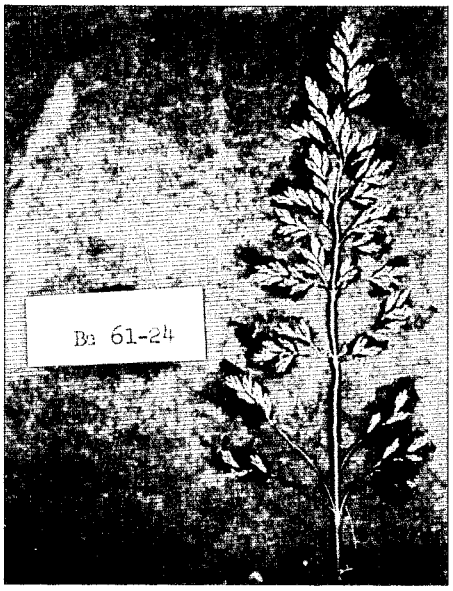
FIG. 2 illustrates a mature panicle of Ba 61–24 Kentucky bluegrass.
Figure 3:
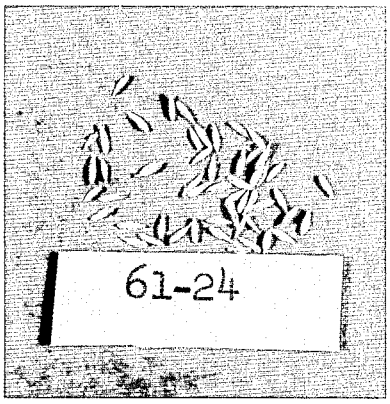
FIG. 3 shows a group of Ba 61–24 Kentucky bluegrass florets.

Ba 61–24 Kentucky bluegrass is characterized by erect tufted culms 20 to 30 inches tall with an average of 24.3 inches at Marysville, Ohio, when undisturbed by clipping (see FIG. 1). The sheaths are somewhat keeled, and the ligule is about 2 mm. long. Blades are soft, flat or folded and are mostly 1.5 to 4 mm. wide with an average width in mowed turf in the range of about 1.76 to about 2.14 mm. Panicles average 114 to 122 mm. in length, are pyramidal or oblong pyramidal, and range from somewhat contracted to open (see FIG. 2). The lowermost branches are arranged in an average of 4.6 whorls per panicle, ascending or spreading, and naked below. Spikelets are crowded with two to seven flowers (a group of Ba 61–24 florets is shown in FIG. 3) and have an average length of 4.29 to 4.55 mm. Lemmas are webbed at the base and pubescent of the lower two-thirds of the keel and the lower half of the marginal nerves. Intermediate nerves are glabrous.

The foregoing description and measurements are based on plants grown at Marysville, Ohio. Since environmental conditions such as climate and soil influence morphological characteristics to some degree, the morphological characteristics described above may vary.

The morphological characteristics of Ba 61–24 and other commercial available bluegrass varieties are compared in Table I.

TABLE I.—MORPHOLOGICAL COMPARISON OF Ba 61-24 AND OTHER BLUEGRASSES

| | Plant height in inches | Florets per spikelet | Glume length in mm. 1st | Glume length in mm. 2nd | Panicle length in mm. | Spikelet length in mm. | Floret length in mm. | Leaf blade width in mm. | Panicle whorl branch |
|---|---|---|---|---|---|---|---|---|---|
| Variety: | | | | | | | | | |
| Ba 61-24 | 24.3 | 6.6–6.8 | 1.94–2.78 | 2.80–3.28 | 114–122 | 4.29–4.55 | 3.73–4.00 | 1.76–2.14 | 4.6 |
| Delta | 30.6 | 4.4–4.6 | 1.85–2.71 | 2.56–3.18 | 103–109 | 3.73–3.95 | 3.06–3.30 | 1.78–1.96 | 4.7 |
| Newport | 26.7 | 4.5–4.7 | 2.32–2.80 | 2.92–3.40 | 82–85 | 4.24–4.48 | 3.79–4.05 | 1.79–1.95 | 3.9 |
| Merion | 21.7 | 4.1–4.3 | 1.90–2.66 | 2.45–3.31 | 99–106 | 3.72–4.04 | 2.88–3.12 | 1.69–1.87 | 4.9 |
| Windsor | 20.6 | 6.8–7.0 | 2.07–2.81 | 3.03–3.13 | 103–112 | 4.55–4.73 | 3.45 3.61 | 1.86–2.00 | 5.7 |

As shown by the foregoing table, the morphological characteristics of Ba 61–24 afford a basis for distinguishing it from other varieties of *Poa pratensis.*

Ba 61–24 Kentucky bluegrass can also be distinguished from other varieties of *Poa pratensis* by a chromatographic analysis of its phenolic constituents. The results of such an analysis are depicted in FIGS. 10–13. In this analysis a sample of Ba 61–24 leaf clippings was extracted with 80% methanol. The 80% methanol extract was concentrated in vacuo and then extracted with petroleum ether to remove chlorophylls, carotenoids, and other fat soluble material. After further concentrating in vacuo this extract was saturated with sodium chloride and extracted with ethyl acetate giving a polyphenol fraction designated as 6–4. The ethyl acetate extracted extract was made alkaline with ammonium hydroxide, and then the rest of the polyphenols were precipitated with lead acetate and regenerated with hydrogen sulfide. This second polyphenol fraction was designated 6–14.

These two fractions were chromatographed by the two-dimensional thin layer technique. More particularly, they were spotted on 20 x 20 cm. plates coated with Avicel microcrystalline cellulose, which were developed first in butanol-acetic acid-water (4:1:5) and after thorough drying then developed in 20% acetic acid and again dryed. The dried chromatograms were sprayed with either 1% diphenylboric acid ethanolamine complex in methanol or 1% aluminum chloride in methanol.

When the sprayed chromatograms were viewed under ultraviolet light, 350 millimicron, the patterns shown in FIGS. 10–13 were observed.[1]

Further, Ba 61–24 Kentucky bluegrass can be distinguished from a number of other varieties of *Poa pratensis* by its floret-caryopsis characteristics. The number of caryopses with attached lemma and palea per pound of Ba 61–24 and other varieties of *Poa pratensis* are given in Table II below. A standard error value calculated for comparing the mean count for Ba 61–24 with each of the other bluegrass varieties shows the mean of Ba 61–24 to differ significantly from Newport, Merion, and Delta. The test of significance indicated no significant difference in the number of caryopses per pound between Ba 61–24, Windsor, and Park varieties of *Poa pratensis*.

TABLE II

Number of Caryopses with attached Lemma and Palea per pound of Ba 61–24 and other Kentucky bluegrasses.

| | Number per pound [1] | Standard error |
|---|---|---|
| Variety: | | |
| Ba 61–24 | 1,792,000 | 15,200 |
| Windsor | 1,805,000 | 5,600 |
| Newport | 2,082,000 | 71,300 |
| Park | 1,757,000 | 65,600 |
| Delta | 1,433,000 | 135,400 |
| Merion | 2,063,000 | 16,500 |

[1] Number per pound is an average based on 3–1 gram samples counted with an Agricultural Specialities electronic seed counter.

As indicated above, one of the outstanding desirable characteristics of Ba 61–24 Kentucky bluegrass is its disease resistance. In this conjunction two causal pathogens responsible for sever and extensive injury to turf in the transistion zone (e.g., in the Washington, D.C. area) are Helminthosporium spp (leaf spot) and *Fusarium roseum*. Leaf spot is most prevalent in the spring and early summer and *Fusarium roseum* most prevalent in mid-summer when day and night temperatures are high.

Figure 8:
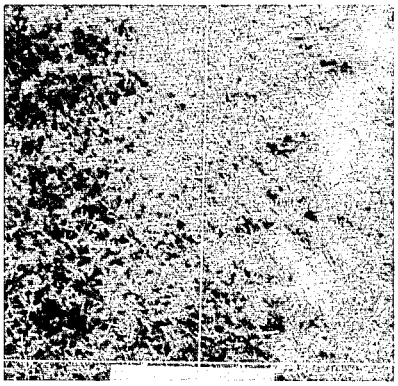
FIG. 8 illustrates the resistance of Ba 61–24 to *Fusarium roseum* as compared to Common Kentucky bluegrass.

At the 5% level there was a significant difference between the resistance of Ba 61–24 and other, commercial varieties to *Fusarium roseum* in Washington, D.C. plots with Ba 61–24 being the more resistant as shown in FIG. 8[2] and in Tables III and IV. This is important since *Fusarium roseum* alone can become so severe as to damage a turf to the extent that it is unable to recover.

TABLE III

Comparison of the susceptibility of Ba 61–24 and other bluegrass varieties to the causal organism *Fursarium roseum*—Washington, D.C. plots in June

Figure 13:
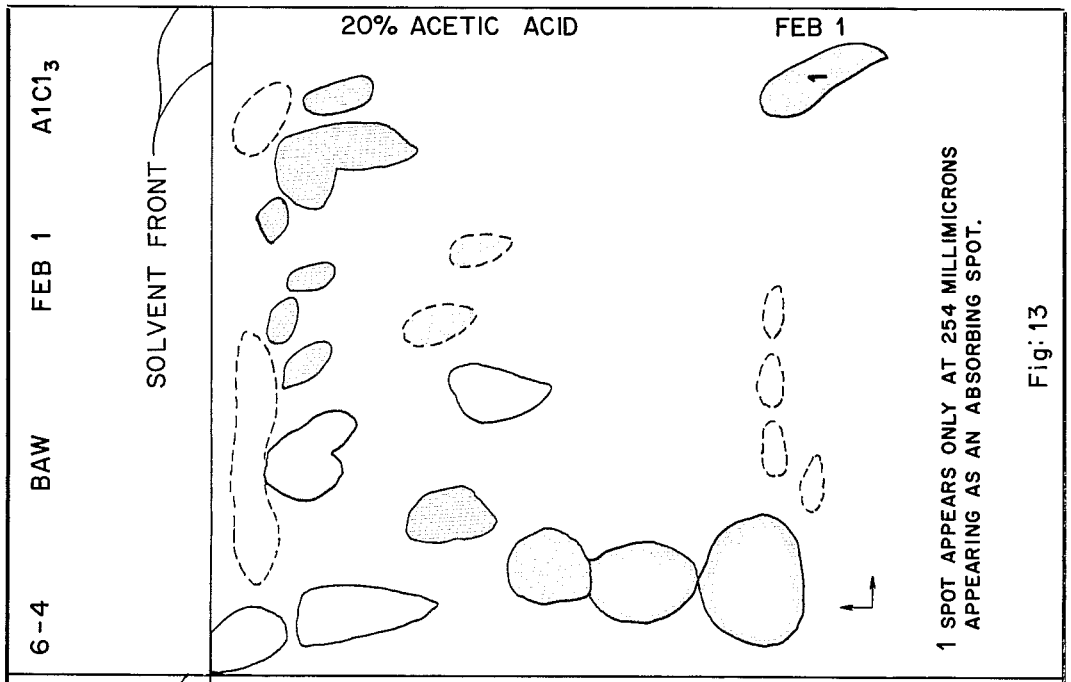
Figure 12:
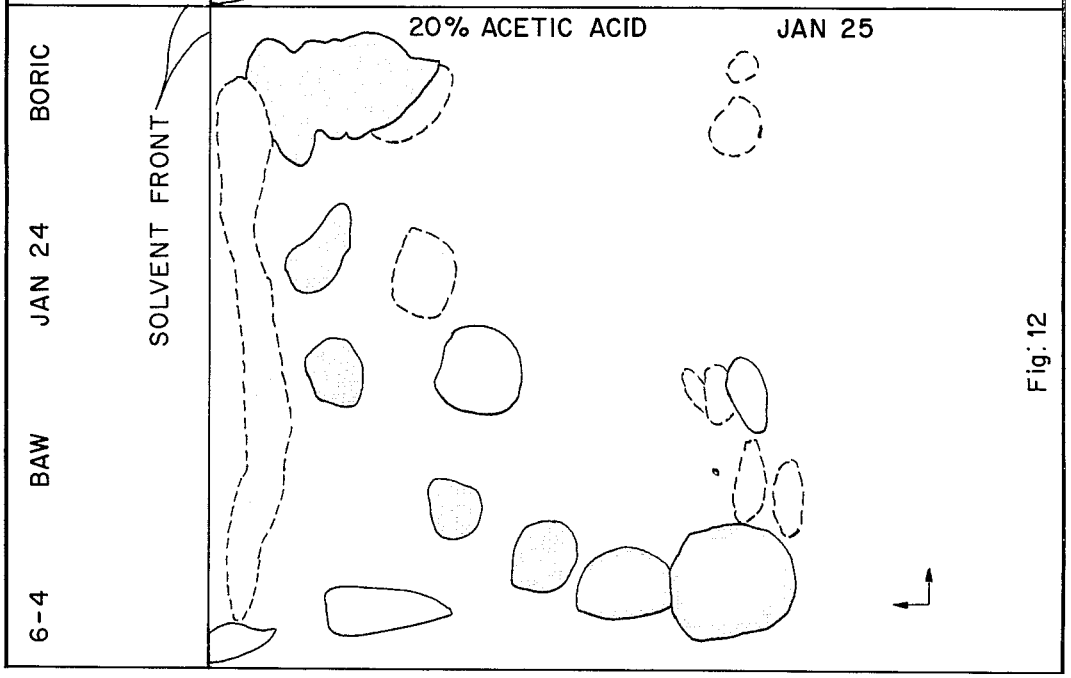

[1] The patterns of FIGS. 10 and 11 differ from those of FIGS.12 and 13 because the polyphenol fractions (6–4 and 6–14, respectively) are different. Similarly, the pattern of FIG. 10 differs from that of FIG. 11 and the pattern of FIG. 12 from the pattern of FIG. 13 because the boric and aluminum chloride sprays detect different compounds.

[2] In FIG. 8 the plot on the left is Ba 61–24 Kentucky bluegrass. The plot on the right is Common Kentucky bluegrass.

| Variety: | Ranking scale,[1] percent |
|---|---|
| Ba 61–24 | 10 |
| Newport | 45 |
| Common Kentucky | 70 |
| Merion | 15 |

[1] Ranking scale: Number indicates percent of disease incidence in plot.

Ethyl extracts of leaf clippings of Merion and Newport were similarly chromatographed. Two-dimensional chromatograms of the Merion- and Newport-ethyl acetate extract sprayed with 1% diphenylboric acid ethanolamine complex or 1% aluminum chloride had two blue spots to the left of the origin; whereas those of the Ba 61–24 ethyl acetate extract had three blue spots to the left of the origin. When two-dimensional chromatograms of these extracts were sprayed with Benedict's reagent, those of the Merion and Newport ethyl acetate extracts had two greenish-yellow spots to the left of the origin; those of the Ba 61–24 ethyl acetate extract had two greenish-yellow spots followed by a blue spot to the left of the origin. Also, the two-dimensional chromatograms of the Ba 61–24 ethyl acetate extract sprayed with Benedict's reagent had an absorption spot in the center of the chromatograms; while those of Merion and Newport did not.

TABLE IV

Comparisons of the susceptibility of Ba 61–24 and other bluegrass varieties to the causal organism *Fursarium roseum*—Washington, D.C. to plots in August

| Variety: | Ranking scale,[1] percent |
|---|---|
| Ba 61–24 | 12.5 |
| Newport | 84.5 |
| Common Kentucky | 75 |
| Merion | 70 |

[1] Ranking scale: Number indicates percent of disease incidence in plot.

Ba 61–24 also has a high level of resistance to Helminthosporium spp. This is shown by the comparative data in Table V.

TABLE V

Comparisons of the susceptibility of Ba 61–24 and other bluegrass varieties to the causal organism Helminthosporium spp—Washington, D.C. in May

| Variety: | Ranking scale,[1] percent |
|---|---|
| Ba 61–24 | 10 |
| Common Kentucky | 80 |
| Newport | 33 |
| Merion | 13 |

[1] Ranking scale: Number indicates percent of disease incidence in plot.

Figure 7:
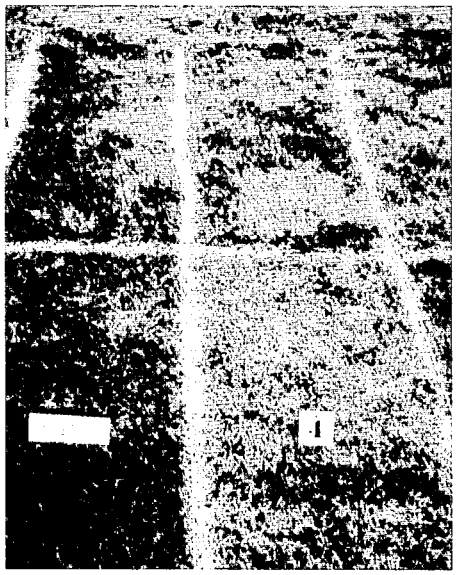
FIG. 7 illustrates the resistance of Ba 61–24 to *Ustilago striiformis* as compared to a susceptible commercial variety.

As mentioned above, Ba 61–24 Kentucky bluegrass is also highly resistant to the causal pathogen *Ustilago striiformis*. This is apparent from FIG. 7 in which the Ba 61–24 (left front plot) is virtually free of the disease and the varieties of *Poa pratensis* in the other plots are infected. The other bluegrasses shown in FIG. 7 are Newport (lower righthand plot), Merion (directly above Newport), and several experimental varieties of Common Kentucky type.

Another attribute of Ba 61–24 Kentucky bluegrass is that its color is equal to or better than that of other varieties of *Poa pratensis*. This is illustrated by the data in Table VI.

TABLE VI

Turf color comparisons for Ba 61–24 and other bluegrass varieties—Washington, D.C. in October

| Variety: | Color rating [1] |
|---|---|
| Ba 61–24 | 9.5 |
| Common Kentucky | 9.0 |
| Newport | 9.5 |
| Merion | 9.0 |

[1] Rating scale: 10=darkest green, 1=lightest green.

Ba 61–24 is also distinguished by its ability to produce a dense turf which is capable of withstanding environmental stresses, both natural and mechanical. These include injury from disease, drought, and heat, and foot and game traffic.

Turf density comparisons for two successive growing seasons in Washington, D.C. are given in Tables VII and VIII.

TABLE VII

| | Rating [1], percent | | |
|---|---|---|---|
| | June | August | October |
| Variety: | | | |
| Ba 61–24 | 90 | 80 | 100 |
| Newport | 60 | 30 | 43 |
| Common Kentucky | 45 | 45 | 70 |
| Merion | 85 | 45 | 75 |

[1] Ranking Scale: Number indicates percent coverage of plot by desirable turf.

TABLE VIII

Turf density comparison of Ba 61–24 and other bluegrass varieties—Washington, D.C. in August

| Variety: | Ranking scale,[1] percent |
|---|---|
| Ba 61–24 | 85 |
| Common Kentucky | 10 |
| Newport | 20 |
| Campus | 10 |

[1] Ranking scale: Number indicates percent coverage of plot by desirable turf.

Of particular importance in Tables VII and VIII is the data showing the markedly superior density of Ba 61–24 Kentucky bluegrass during hot summer months (June and especially August). This again demonstrates the adaptability of Ba 61–24 to high temperatures and its resistance to turf disease organisms.

Figure 6:
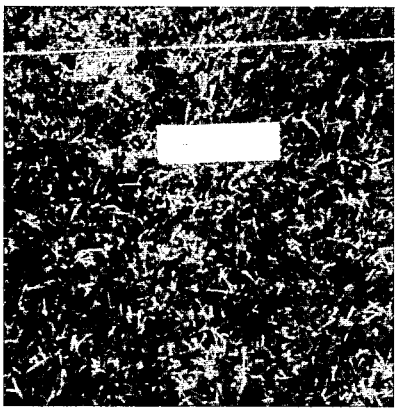
FIG. 6 illustrates the performance of Ba 61–24 in August at Washington, D.C.
Figure 9:
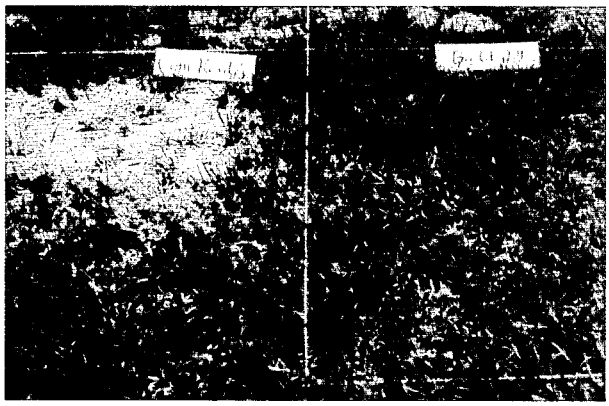
FIG. 9 illustrates turf performance of Ba 61–24 under high temperatures in August at Washington, D.C.

FIGS. 6 and 9 are photographs of Ba 61–24 Kentucky bluegrass in Washington, D.C in August of the year in which the data tabulated in Table VII was collected (FIG. 9) and in August of the year in which the data of Table VIII (FIG. 6) was gathered. As shown by these figures, the turf was healthy, vigorous and of much higher quality than that produced by the other varieties shown under the environmental stresses existent in summer months.

Table IV demonstrates the ability of Ba 61–24 Kentucky bluegrass to withstand mowing at the abnormally low heights of one inch and one-half inch.[3] This data further demonstrates the ability of Ba 61–24 to tolerate and adapt itself to unusual environmental stresses.

The tests from which the data in FIG. 9 was obtained spanned a period of two years. The turf was mowed weekly.

TABLE IX

Turf density of Ba 61–24 at Marysville, Ohio in October.

| | Rating [1], percent | |
|---|---|---|
| | Mowing Ht. 1" | Mowing Ht. ½" |
| Variety: | | |
| Ba 61–24 | 100 | 95 |

[1] Rating scale: Number indicates percent coverage of plot by desirable turf.

[3] Recommended mowing heights for bluegrasses are two to three inches.

Figure 4:
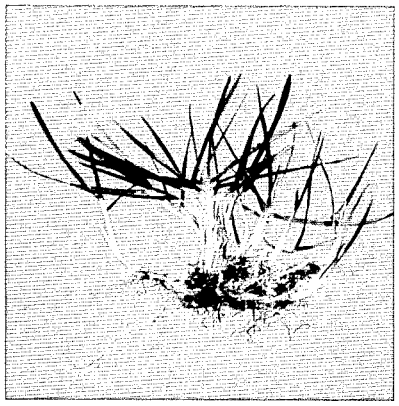
FIG. 4 illustrates the robust rhizome formation of Ba 61–24 Kentucky bluegrass.
Figure 5:
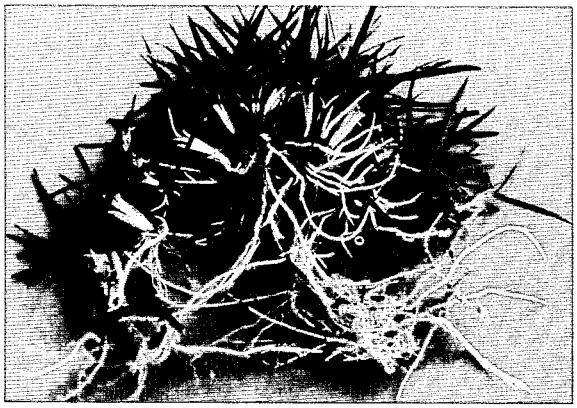
FIG. 5 illustrates tillering of Ba 61–24 Kentucky bluegrass plant.

Related important and distinguishing attributes of Ba 61–24 Kentucky bluegrass are its vigor and the rapidity with which it reproduces. In comparative sprigging tests with other, commercially available bluegrasses Ba 61–24 was consistently the first to fill in the bare areas and reach 100% density (this is important since the rapid spreading of Ba 61–24 makes it difficult for undesirable grasses and other weeds to become established in sprigged plots). This highly desirable characteristic of Ba 61–24 is attributable to superior rhizome formation (see FIG. 4) and tillering (see FIG. 5) and to the superior, robust nature of sprigged Ba 61–24 plants demonstrated by the data in the following table.

TABLE X

Comparative turf vigor of sprigged Ba 61–24 and other bluegrass varieties at Washington, D.C.

| | Rating [1] | | |
|---|---|---|---|
| | June | August | October |
| Variety: | | | |
| Ba 61–24 | 2.5 | 2.5 | 2.8 |
| Merion | 2 | 1.5 | 1.5 |

[1] Ranking scale: 3=strong vigor; 1=poor vigor.

The various turf and turfgrass characteristics described above are all taken into account in determining what is known as a "turf quality rating." Great significance is attached to this rating because it is indicative of the general appearance, uniformity, and asthetic value of a turf and because, as just indicated, all of the performance characteristics of the grass are taken into consideration so that a good turf rating is an indication that the grass is free of disease, has good color, density, uniformity, and an acceptable texture and is pleasing to walk on.

The data in Tables XI–XV demonstrates the superiority of Ba 61–24 over other, commercially available varieties in turf quality ranking. More specifically, Table XI shows the rating of one year old turfs at Marysville, Ohio with Ba 61–24 having by far the highest rating. Table XII shows turf quality performance at different times of the year at the same location for two year old turfs. Again, Ba 61–24 turf consistently exhibited higher quality in both cases.

Tables XIII–XV are ratings for turf grown in the Washington, D.C. area for three successive years at different times throughout the growing season. Of particular interest is the data showing the markedly superior quality of Ba 61–24 turf during the hot summer months in which bluegrass is notorious for its poor performance.

TABLE XI

Turf quality comparisons of Ba 61–24 and other bluegrass varieties at Marysville, Ohio in October

| Variety: | Quality rating [1] |
|---|---|
| Ba 61–24 | 4 |
| Common Kentucky | 2 |
| Newport | 1.5 |
| Merion | 3.5 |
| Delta | 2 |

[1] Ranking scale: 4=excellent turf, 1=poorest turf.

TABLE XII

Turf quality comparisons of Ba 61–24 and other bluegrass varieties at Marysville, Ohio.

| | Quality Rating [1] | |
|---|---|---|
| | July | October |
| Variety: | | |
| Ba 61–24 | 4 | 4 |
| Common Kentucky | 2 | 1.5 |
| Delta | 2 | 1.5 |
| Newport | 1.5 | 2 |
| Merion | 3 | 3 |

[1] Ranking scale: 4=excellent turf; 1=poorest truf.

TABLE XIII

Turf quality comparisons for Ba 61–24 and other bluegrass varieties at Washington, D.C. in October

| Variety: | Quality rating [1] |
|---|---|
| Ba 61–24 | 4 |
| Common Kentucky | 1.5 |
| Newport | 3.5 |
| Merion | 2.0 |

[1] Ranking scale: 4=excellent turf, 1=poorest turf.

TABLE XIV

Turf quality comparisons of Ba 61–24 and other bluegrass varieties at Washington, D.C.

| | Quality Rating [1] | |
|---|---|---|
| | August | October |
| Variety: | | |
| Ba 61–24 | 4 | 4 |
| Newport | 1 | 1 |
| Common Kentucky | 1 | 1 |
| Merion | 1 | 1 |

[1] Ranking scale: 4=excellent turf; 1=poorest turf.

TABLE XV

Turf quality comparisons of Ba 61–24 and other bluegrass varieties at Washington, D.C.

| | Ranking Scale [1] | | |
|---|---|---|---|
| | June | August | October |
| Variety: | | | |
| Ba 61–24 | 3 | 4 | 4 |
| Merion | 1.5 | 3 | 3 |
| Common Kentucky | 1 | 1 | 1 |
| Newport | 1 | 1 | 1 |

[1] Ranking scale: 4=excellent turf; 1=poorest turf.

In short the data in the preceding tables shows that Ba 61–24 Kentucky bluegrass can be readily distinguished from other, commercially available varieties by the excellent quality of the turf it produces, especially under conditions of high environmental stress.

What is claimed and desired to be secured by Letters Patent is:

1. A variety of *Poa pratensis* substantially as shown and described herein.

No references cited.

ROBERT E. BAGWILL, Primary Examiner